(12) United States Patent
Marshall

(10) Patent No.: US 7,690,917 B2
(45) Date of Patent: Apr. 6, 2010

(54) BRACKET ALIGNMENT DEVICE

(75) Inventor: Michael C. Marshall, Prior Lake, MN (US)

(73) Assignee: GeoDigm Corporation, Chanhassen, MN (US)

( * ) Notice: Subject to any disclaimer, the term of this patent is extended or adjusted under 35 U.S.C. 154(b) by 161 days.

(21) Appl. No.: 11/893,985

(22) Filed: Aug. 17, 2007

(65) Prior Publication Data
US 2008/0227050 A1 Sep. 18, 2008

Related U.S. Application Data

(60) Provisional application No. 60/838,653, filed on Aug. 17, 2006.

(51) Int. Cl.
*A61D 5/00* (2006.01)
(52) U.S. Cl. .................................. 433/3; 433/2; 433/72
(58) Field of Classification Search ...................... 433/2, 433/3, 24, 229, 72; 700/98; 604/116
See application file for complete search history.

(56) References Cited

U.S. PATENT DOCUMENTS

| | | | |
|---|---|---|---|
| 4,575,805 A | 3/1986 | Moermann et al. | |
| 4,611,288 A | 9/1986 | Duret et al. | |
| 4,837,732 A | 6/1989 | Brandestini et al. | |
| 5,113,424 A | 5/1992 | Burdea et al. | |
| 5,267,293 A | 11/1993 | Virta | |
| 5,273,429 A | 12/1993 | Rekow et al. | |
| 5,343,391 A | 8/1994 | Mushabac | |
| 5,347,454 A | 9/1994 | Mushabac | |
| 5,368,478 A | 11/1994 | Andreiko et al. | |
| 5,372,502 A | 12/1994 | Massen et al. | |
| 5,416,822 A | 5/1995 | Kunik | |
| 5,431,562 A | 7/1995 | Andreiko et al. | |
| 5,448,472 A | 9/1995 | Mushabac | |
| 5,518,397 A | 5/1996 | Andreiko et al. | |
| 5,533,895 A | 7/1996 | Andreiko et al. | |
| 5,549,476 A | 8/1996 | Stern | |
| 5,569,578 A | 10/1996 | Mushabac | |
| 5,588,430 A | 12/1996 | Bova et al. | |
| 5,605,459 A | 2/1997 | Kuroda et al. | |
| 5,879,158 A | 3/1999 | Doyle et al. | |
| 6,068,482 A | 5/2000 | Snow | |
| 6,123,544 A | 9/2000 | Cleary | |

(Continued)

OTHER PUBLICATIONS

Hayashi, T. et al. "A Computerized System for Analyzing Occlusal Relations During Mandibular Movements," *The Intl. Journal of Prosthodontics*, vol. 7, No. 2, pp. 108-114 (Mar./Apr. 1994).

*Primary Examiner*—Ralph A Lewis
*Assistant Examiner*—Eric Rosen
(74) *Attorney, Agent, or Firm*—Merchant & Gould P.C.

(57) ABSTRACT

A method includes obtaining an electronic model image representing teeth of a patient; determining a desired bracket arrangement for one or more brackets on the teeth; designing an electronic model image of an alignment device based in part on the desired bracket arrangement; and fabricating the alignment device based on the electronic model image of the alignment device. The desired bracket arrangement includes a surface location, a tip orientation, and a torque orientation of each bracket. The alignment device defines at least one slot through which a bracket can be placed at a surface location and an orientation indicator to indicate a desired tip orientation and a desired torque orientation of each bracket.

12 Claims, 15 Drawing Sheets

U.S. PATENT DOCUMENTS

| | | |
|---|---|---|
| 6,143,003 A | 11/2000 | Cosman |
| 6,322,359 B1 | 11/2001 | Jordan et al. |
| 6,371,761 B1 | 4/2002 | Cheang et al. |
| 6,409,504 B1 | 6/2002 | Jones et al. |
| 6,450,807 B1 | 9/2002 | Chishti et al. |
| 6,554,613 B1 | 4/2003 | Sachdeva et al. |
| 6,632,089 B2 | 10/2003 | Rubbert et al. |
| 6,648,640 B2 | 11/2003 | Rubbert et al. |
| 6,688,886 B2 | 2/2004 | Hughes et al. |
| 6,905,337 B1 | 6/2005 | Sachdeva |
| 7,214,056 B2 * | 5/2007 | Stockstill ........................ 433/3 |
| 2003/0224316 A1 | 12/2003 | Marshall |
| 2004/0029078 A1 | 2/2004 | Marshall |
| 2004/0066877 A1 | 4/2004 | Arai et al. |
| 2005/0239013 A1 * | 10/2005 | Sachdeva .................... 433/24 |

\* cited by examiner

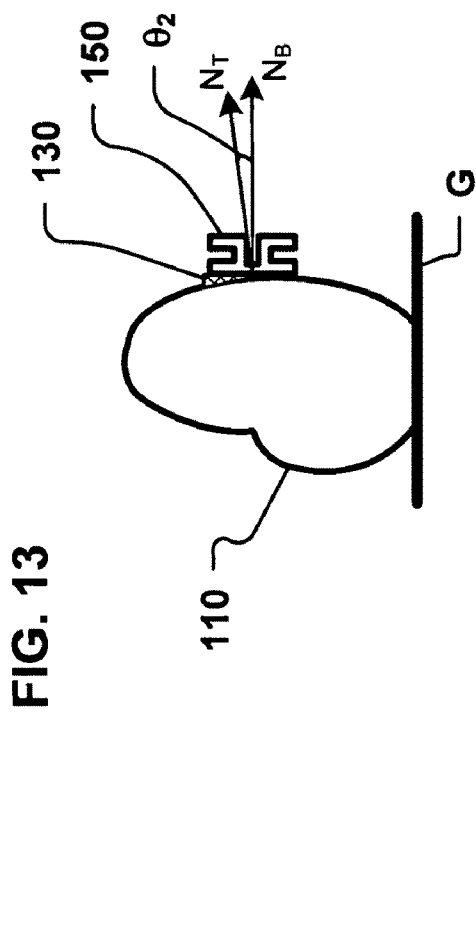
FIG. 12
FIG. 13
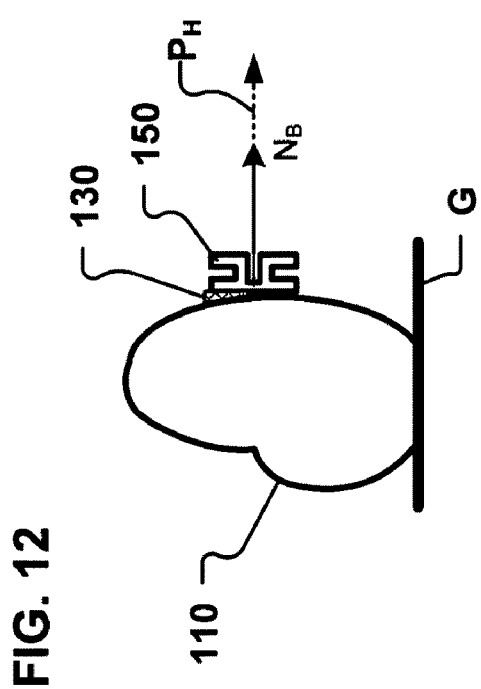
FIG. 16

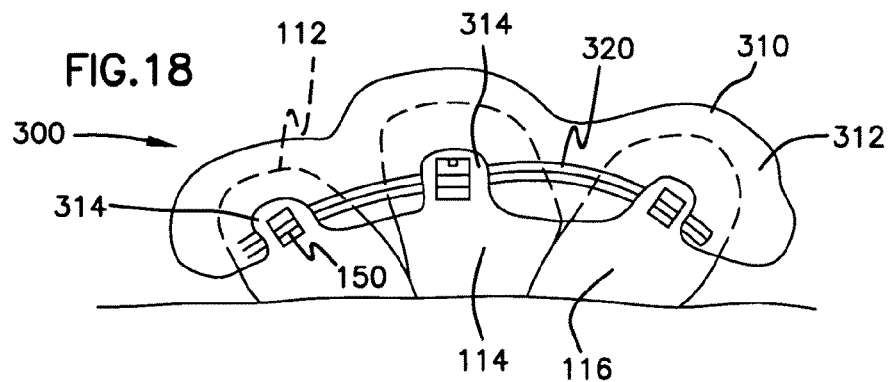
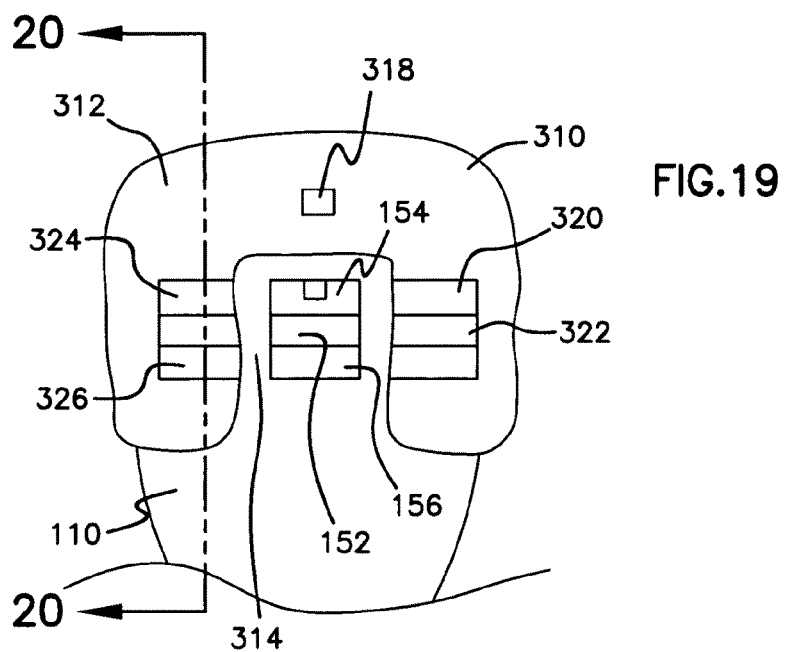
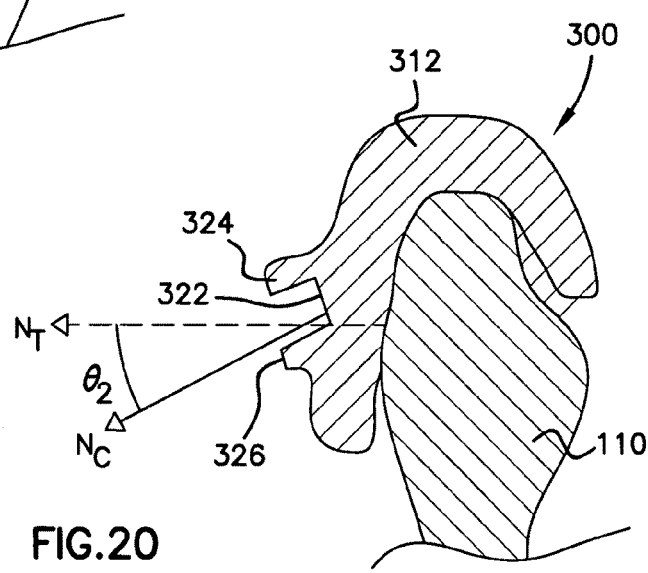

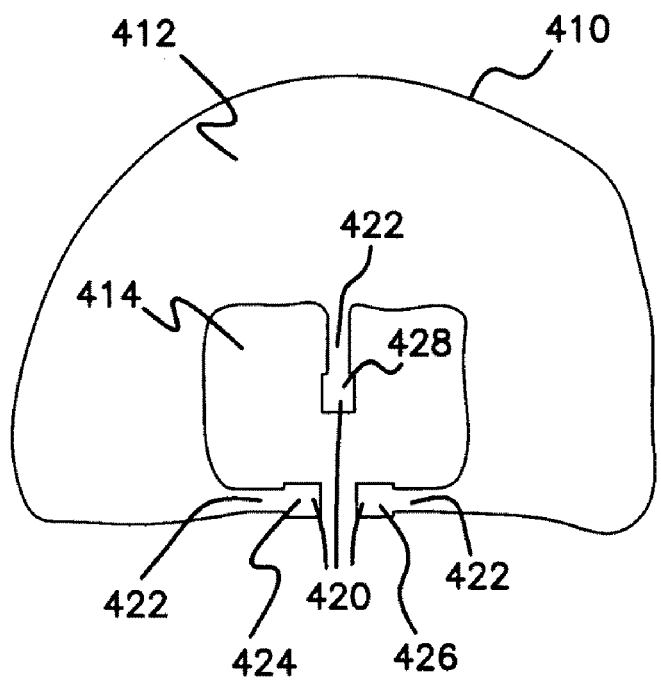
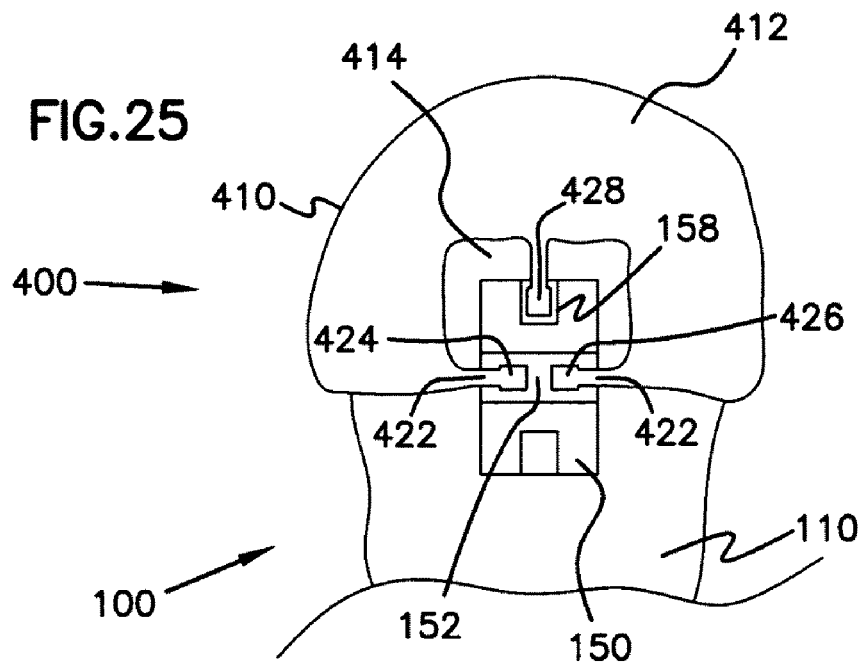

BRACKET ALIGNMENT DEVICE

CROSS REFERENCE TO RELATED APPLICATION

This application claims priority from provisional application Ser. No. 60/838,653, filed Aug. 17, 2006, and which is incorporated herein by reference.

TECHNICAL FIELD

The invention relates generally to a method, system, and device for positioning brackets on teeth; and, more particularly, to bracket alignment devices, and systems and methods for producing and utilizing the same.

BACKGROUND

Brackets are typically bonded to teeth for the purpose of orthodontic treatment. One method of securing the brackets to the teeth of a patient includes applying adhesive to the brackets and manually placing the brackets directly on the patient's teeth. Another method involves manually placing the brackets on a dental model of the patient's teeth, transferring the brackets from the dental model to a bonding tray, and then transferring the brackets from the tray to the correct locations on the patient's teeth. This latter method is commonly known as indirect bonding. While indirect bonding generally provides an accurate location of the brackets based on the bracket positions on the model, dental technicians must still position the brackets onto the model by manually estimating or "eyeballing" the correct positions. Such techniques, therefore, are prone to human error.

There arises a need in the art to provide systems and methods for accurately securing brackets onto desired positions on a patient's teeth.

SUMMARY

The present invention provides for devices, systems, and methods for securing brackets to the correct locations, and in the correct orientations, on a patient's teeth. In particular, the invention relates to bracket location and alignment devices, and systems and methods of designing, fabricating and utilizing the same.

In general, a dental/orthodontic professional plans a course of treatment for shifting one or more teeth of the patient into desired positions based on manipulation of electronic model images of the patient's teeth. Desired locations for brackets are determined using the electronic models. In a preferred embodiment, the desired locations are determined based on the desired positions of the teeth post-treatment.

An electronic model of an alignment device can be designed based on the electronic model images of the patient's teeth and the desired bracket locations. The alignment device can be fabricated based on the electronic model and used to properly position the brackets, either directly or indirectly, on the teeth of the patient.

The alignment device generally defines a body and at least one slot through which a bracket can be placed at a surface location. The alignment device also includes an orientation indicator to denote a desired tip orientation and a desired torque orientation of the bracket. Typically, the orientation indicator is coupled to the body adjacent the slot. The alignment device can also include an alignment tool configured to align the bracket with the orientation indicator when the bracket is positioned at the location on the surface through the slot.

According to one aspect, the alignment device is configured to aid in securing brackets to a dental cast to aid with indirect bonding. Such an alignment device typically includes an alignment tool to aid in positioning the brackets.

According to another aspect, the alignment device is configured to aid in directly bonding brackets to a patient's teeth. Such an alignment device typically includes fingers configured to retain one or more brackets in a fixed position.

In a preferred alignment method, an electronic model image representing the teeth of a patient is obtained; and a desired bracket arrangement is determined for one or more brackets on the teeth of the electronic model image. The desired bracket arrangement includes a surface location, a tip orientation, and a torque orientation of each bracket. The method also includes designing an electronic model image of an alignment device based in part on the desired bracket arrangement; and fabricating the alignment device based on the electronic model image.

In a preferred embodiment, the alignment system can include a three-dimensional scanner; a computing system; and a rapid prototyping device. The scanner digitizes one or more dental casts to generate electronic model images of the dental casts. The computing system enables display, manipulation, storage, and transmission of the electronic model images. The computing system also enables the user to design an electronic model of an alignment device configured to aid in properly locating and aligning the brackets on the patient's teeth. The rapid prototyping device enables fabrication of the alignment device based on the electronic model.

While the invention will be described with respect to preferred embodiment configurations and with respect to particular devices used therein, it will be understood that the invention is not to be construed as limited in any manner by either such configuration or components described herein. Also, while the particular types of scanning devices, computing devices, and fabrication devices used in the preferred embodiment are described herein, it will be understood that such particular components are not to be construed in a limiting manner. Instead, the functionality of those devices should be appreciated. These and other variations of the invention will become apparent to those skilled in the art upon a more detailed description of the invention.

The advantages and features which characterize the invention are pointed out with particularity in the claims annexed hereto and forming a part hereof. For a better understanding of the invention, however, reference should be had to the drawing which forms a part hereof and to the accompanying descriptive matter, in which there is illustrated and described a preferred embodiment of the invention.

BRIEF DESCRIPTION OF THE DRAWINGS

Referring to the drawing, wherein like numerals represent like parts throughout the several views:

FIG. 12 illustrates the normal vector of a bracket mounted to a post-treatment tooth relative to a generally horizontal plane according to one embodiment of the present disclosure;

FIG. 13 illustrates the torque orientation of the bracket of FIG. 12 relative to the normal vector of the tooth according to one embodiment of the present disclosure;

FIG. 16 illustrates the torque orientation of a bracket mounted to a pre-treatment tooth relative to the normal vector of the tooth according to one embodiment of the present disclosure;

FIG. 18 is a front view of a first alignment device mounted to teeth arranged in pre-treatment positions according to one embodiment of the present disclosure;

FIG. 19 is a front view of a bracket positioned relative to another type of first alignment device according to one embodiment of the present disclosure;

FIG. 20 is a cross-sectional view of a first alignment device taken along the line 20-20 of FIG. 19 according to one embodiment of the present disclosure;

FIG. 24 is a front view of an example second alignment device including features that are examples of inventive aspects in accordance with the principles of the present disclosure;

FIG. 25 is a front view of the second alignment device of FIG. 24 holding a bracket to a tooth according to one embodiment of the present disclosure;

DETAILED DESCRIPTION

The present disclosure provides for an alignment device for securing brackets to desired locations, and in desired orientations, on a patient's teeth to implement a course of treatment planned by a dental/orthodontic professional. In particular, the disclosure relates to bracket alignment devices and systems and methods for creating and using the same.

Figure 1:
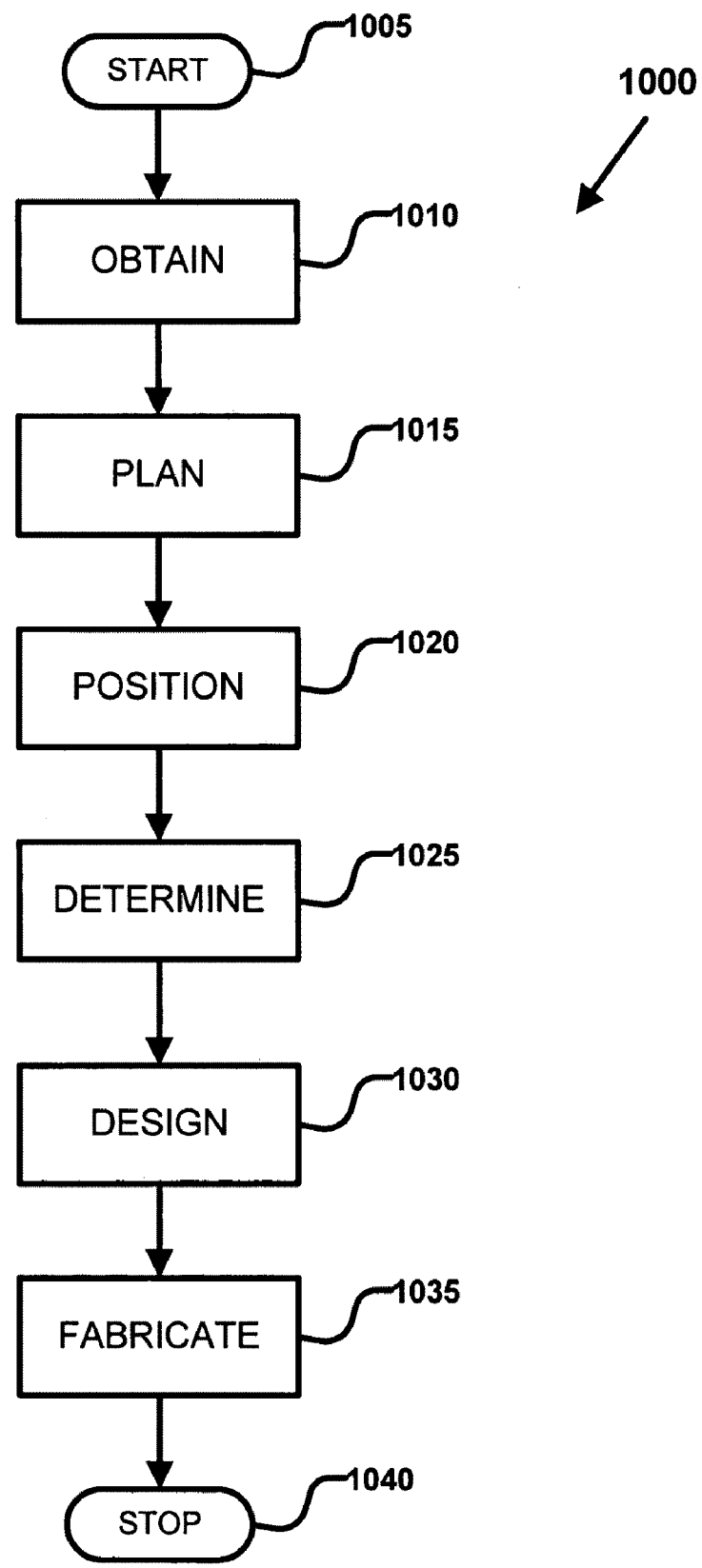
FIG. 1 illustrates an operational flow for a process for creating an alignment device according to one embodiment of the present disclosure.
Figure 2:
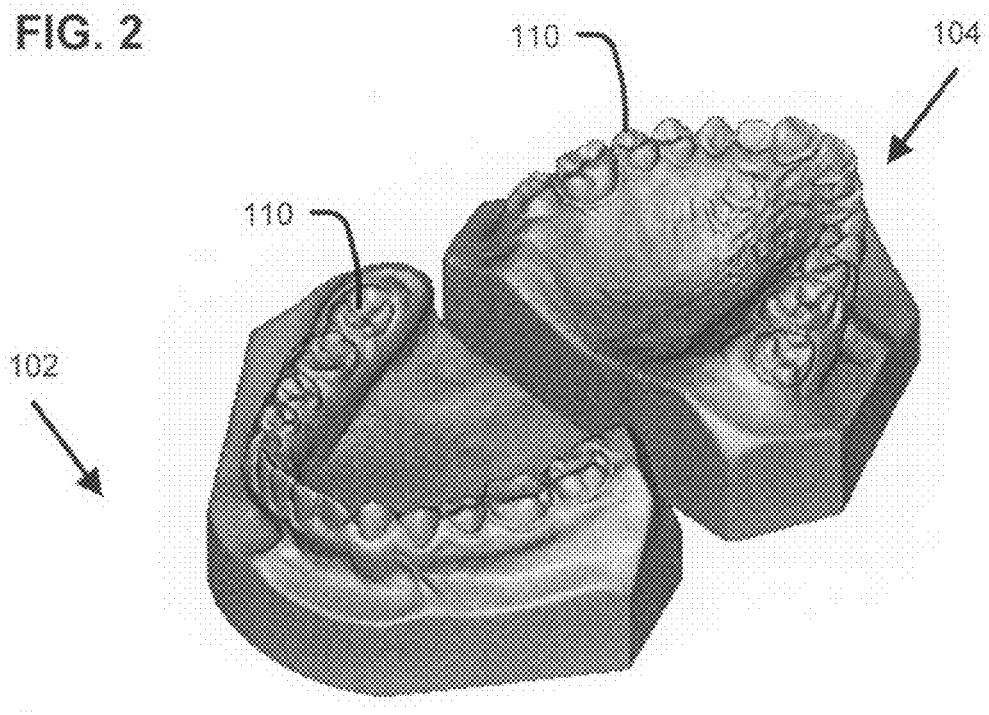
FIG. 2 is a perspective view of an electronic model representing the dental arches of the mandible and the maxilla according to one embodiment of the present disclosure.

Referring to the figures in general, the professional can plan a course of treatment for a patient using one or more electronic models 100 of the patient's dentition. FIG. 1 illustrates an operational flow for a process 1000 for creating one example of an alignment device. The process 1000 begins at start operation 1005 and proceeds to obtain operation 1010. The obtain operation 1010 acquires an electronic model 100 of the patient's dentition (e.g., see FIG. 2).

Figure 3:
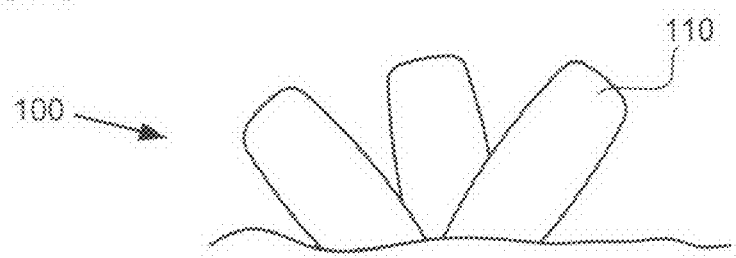
FIG. 3 is a front view of teeth arranged in pre-treatment positions according to one embodiment of the present disclosure.

The electronic model 100 generally represents the teeth 110 of the patient in a pre-treatment arrangement (e.g., see FIG. 3). In some embodiments, the electronic model 100 represents the teeth 110 located on one of the mandible 102 and the maxilla 104 of the patient. In other embodiments, however, the electronic model 100 can represent the teeth 110 located on both the mandible 102 and the maxilla 104. In certain embodiments, the electronic model 100 is formed from a polygonal mesh. In a preferred embodiment, the electronic model 100 is formed from a triangular polygonal mesh. In other embodiments, however, other types of electronic models, such as voxel-based models, can be used.

In some embodiments, the obtain operation 1010 acquires the electronic model 100 by scanning a dental cast of the patient's dentition to obtain spatial data representing the teeth 110 of the patient and generating the electronic model 100 based on the obtained spatial data. In other embodiments, the obtain operation 1010 acquires the electronic model 100 by directly scanning the teeth 110 of the patient or by scanning a bite impression. In still other embodiments, however, the obtain operation 1010 can receive the electronic model 100 from a secondary source.

Figure 4:
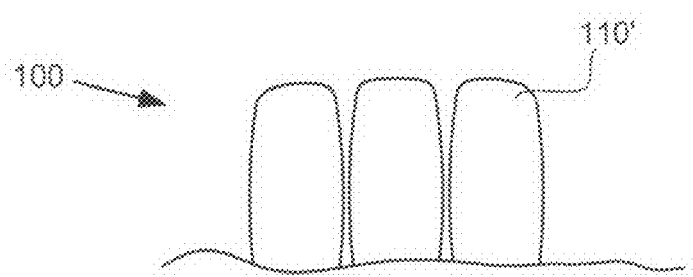
FIG. 4 is a front view of teeth arranged in post-treatment positions according to one embodiment of the present disclosure.

A plan operation 1015 shifts the teeth 110 of the electronic model 100 from the pre-treatment arrangement into desired positions in a post-treatment arrangement (e.g., see FIG. 4). For clarity, teeth arranged in a post-treatment arrangement will be designated as 110'. A position operation 1020 selects desired locations for brackets 150 (see FIG. 9) along the surface of the post-treatment arrangement of the teeth 110' of the electronic model 100 (see FIG. 11). One example process for selecting the desired bracket locations will be discussed in more detail herein with reference to FIG. 10.

Figure 15:
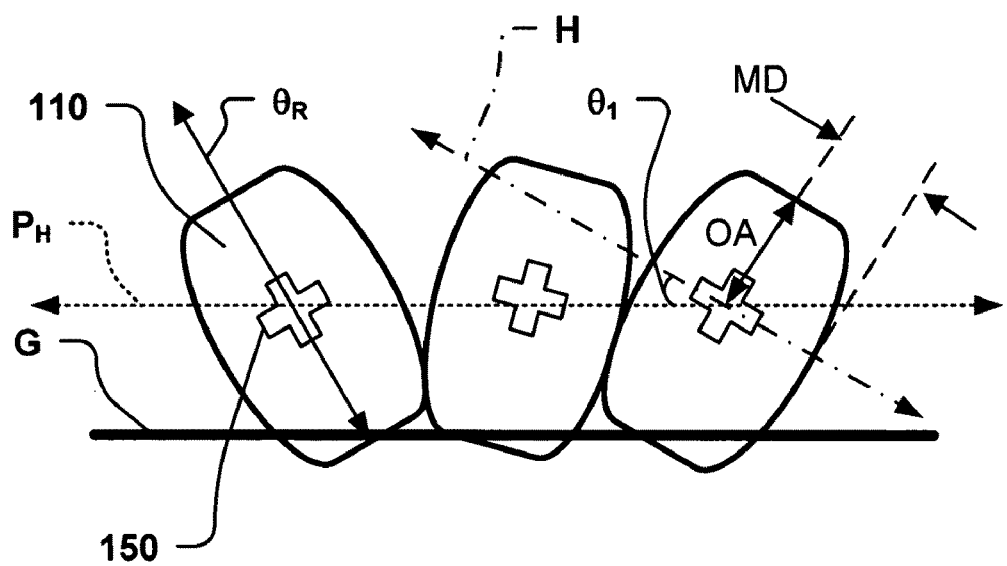
FIG. 15 is a front view of brackets mounted to teeth arranged in pre-treatment positions according to one embodiment of the present disclosure.

When the desired bracket positions are known for the post-treatment arrangement of teeth 110', a determine operation 1025 determines desired bracket locations for the pre-treatment arrangement of the teeth 110 (e.g., see FIG. 15). Next, a design operation 1030 generates an electronic model of an alignment device (e.g., see FIGS. 19 and 24). In general, the electronic model of the alignment device is based on the desired bracket positions for the pre-treatment arrangement of the patient's teeth 110. In certain embodiments, the electronic model of the alignment device is also generated based on desired post-treatment positions of the teeth 110' of the electronic model 100. More details regarding example alignment devices will be provided herein with reference to FIGS. 17-29.

Still referring to FIG. 1, a fabricate operation 1035 produces an alignment device based on the electronic model of the alignment device. In certain embodiments, the fabricate operation 1035 prints out the alignment device on a rapid prototyping machine. In other embodiments, however, the fabricate operation 1035 can produce the alignment device using any desired fabrication process. The fabricated alignment device can be used to properly position the brackets 150. The process ends at stop operation 1040.

Figure 5:
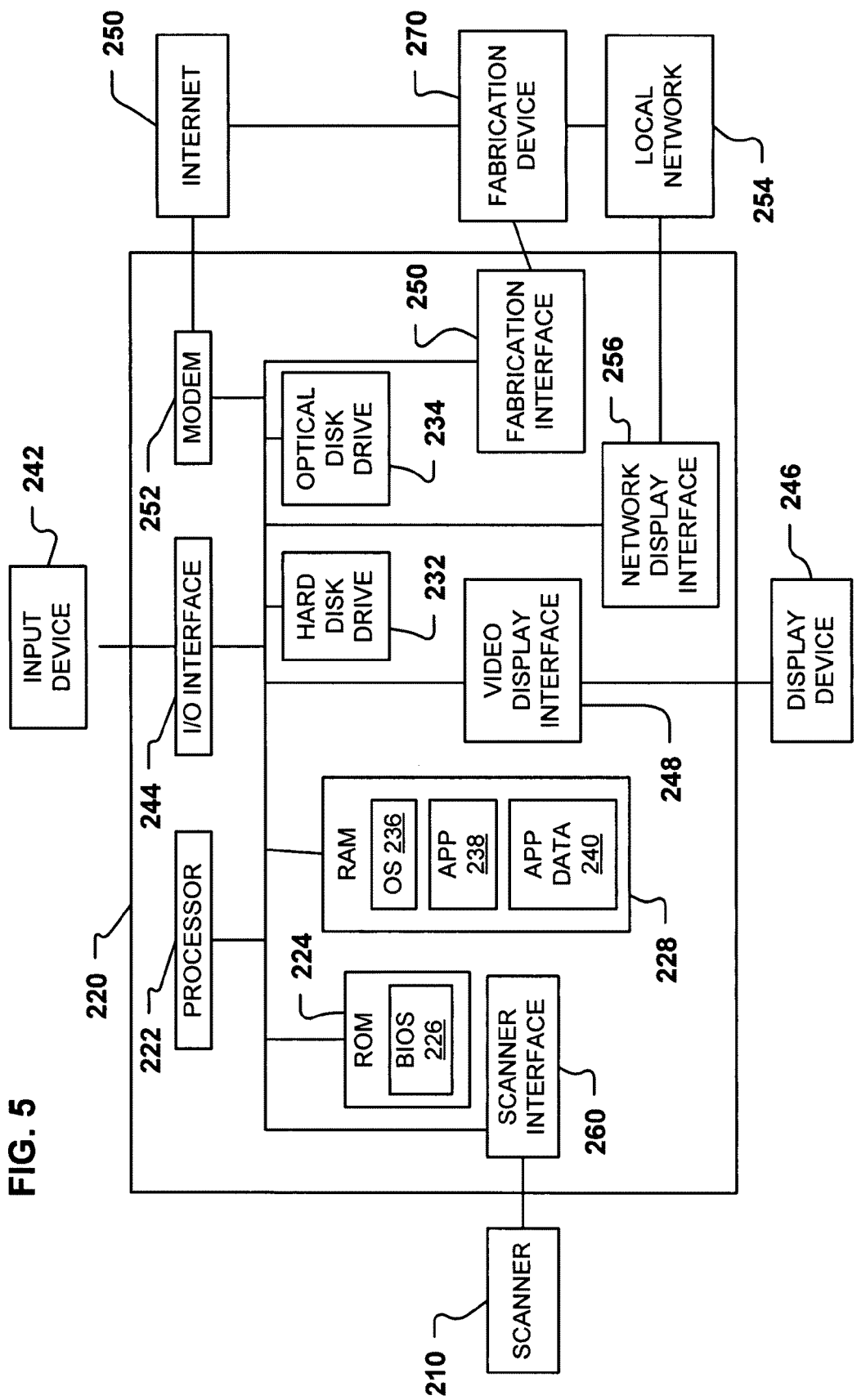
FIG. 5 illustrates an example design and production system on which example processes of the present disclosure can be executed according to one embodiment of the present disclosure.

FIG. 5 illustrates an example design and production system 200 on which example processes of the present disclosure can be executed. In general, the system 200 includes a computing system 220 and a fabrication device 270 coupled to the computing system 220. The computing system 220 is configured to implement at least the design operation 1030 of FIG. 1. In a preferred embodiment, the computing system 220 is configured to implement the plan, position, determine, and design operations 1010-1030. The fabrication device 270 is configured to implement the fabricate operation 1035 of FIG. 1 to produce (e.g., print) objects based on the electronic models generated by the computing system 220.

One example of the computing system 220 includes a processor unit 222, read only memory (ROM) 224, random access memory (RAM) 228, and a system bus 230 that couples various system components including the RAM 228 to the processor unit 222. The system bus 230 may be any of several types of bus structures including a memory bus or memory controller, a peripheral bus and a local bus using any of a variety of bus architectures. A basic input/output system 226 (BIOS) is stored in ROM 224. The BIOS 226 contains basic routines that help transfer information between elements within the computing system 220.

The computing system 220 further includes a hard disk drive 232 for reading from and writing to a hard disk, a magnetic disk drive (not shown) for reading from or writing to a removable magnetic disk, and an optical disk drive 234 for reading from or writing to a removable optical disk, such as a CD-ROM, DVD, or other type of optical media. The hard disk drive 232, magnetic disk drive, and optical disk drive 234 can be connected to the system bus 230 by a hard disk drive interface (not shown), a magnetic disk drive interface (not shown), and an optical drive interface (not shown), respectively. The drives and their associated computer-readable media provide nonvolatile storage of computer readable instructions, data structures, programs, and other data for the computing system 220.

Although the exemplary environment described herein employs a hard disk drive 232, a removable magnetic disk, and removable optical disk drive 234, other types of computer-readable media capable of storing data can be used in the exemplary system. Examples of these other types of computer-readable mediums that can be used in the exemplary operating environment include magnetic cassettes, flash memory cards, digital video disks, and Bernoulli cartridges.

A number of program modules may be stored on the ROM 224, RAM 228, hard disk drive 232, magnetic disk drive, or optical disk drive 234, including an operating system 236, one or more application programs 238, other program modules, and program (e.g., application) data 240.

A user may enter commands and information into the computing system 220 through input devices 242, such as a keyboard, touch screen, and/or mouse (or other pointing device). Examples of other input devices may include a microphone, joystick, game pad, satellite dish, and document scanner. These and other input devices are often connected to the processing unit 222 through an I/O port interface 244 that is coupled to the system bus 230. Nevertheless, these input devices 242 also may be connected by other interfaces, such as a parallel port, game port, or a universal serial bus (USB). A monitor 246 or other type of display device is also connected to the system bus 230 via an interface, such as a video adapter 248. In addition to the display device 246, computing systems typically include other peripheral output devices (not shown), such as speakers and document printers.

The computing system 220 may operate in a networked environment using logical connections to one or more remote computers. Examples of remote computers include personal computers, servers, routers, network PC's, peer devices and other common network nodes, and typically include many or all of the elements described above relative to the computing system 220. In certain embodiments, the network connections can include a local area network (LAN) or a wide area network (WAN). Such networking environments are commonplace in offices, enterprise-wide computer networks, intranets, and the Internet 250.

When used in a WAN networking environment, the computing system 220 typically includes a modem 252 or other means for establishing communications over the wide area network, such as the Internet 250. The modem 252, which may be internal or external, can be connected to the system bus 230 via the I/O port interface 244. When used in a LAN networking environment, the computing system 220 is connected to the local network 254 through a network interface or adapter 256. In a networked environment, program modules depicted relative to the computing system 220, or portions thereof, may be stored in the remote memory storage device. It will be appreciated that the network connections shown are exemplary and other means of establishing a communications link between the computers may be used.

In certain embodiments, the fabrication device 270 includes a rapid prototyping machine configured to print wax patterns. Examples of such a rapid prototyping machine are the SLA® systems produced by 3D Systems of Rock Hill, S.C. However, any type of fabrication device 270 may be used without deviating from the spirit and scope of the disclosure. In certain embodiments, the fabrication device 270 can be connected to the computing system 220 via an appropriate interface 258.

The interface 258 can connected to the bus 230 such that the electronic model data may be retrieved from the appropriate or desired memory location. In some embodiments, the interface 258 converts the electronic models generated on the computing system 220 to a format readable by the fabrication device 270. In one example embodiment, the interface 258 converts the electronic model to an STL file. The converted file can be transmitted to the fabrication device 270 using a direct line connection or using a networked connection described above.

In certain embodiments, the design and production system 200 also includes a scanner 210 configured to implement the obtain operation 1010 of FIG. 1. For example, a three-dimensional scanner 210 can be coupled to the computing system 220 via an appropriate scanner interface 260. The scanner interface 260 is connected to the bus 230 such that the scanned data may be stored in the appropriate or desired memory location, manipulated by the CPU 222, displayed on the display device 246, etc. Preferred scanners include a laser line scanner arranged and configured for scanning line study casts (e.g., plaster casts), such as the dental scanner manufactured by GeoDigm Corporation of Minnesota. The operation and scanning methodology used by such a line scanner is generally described in U.S. Pat. No. 6,217,334. However, any suitable scanner 210 may be used and a number of other methodologies might be employed to generate the scanned image data.

Portions of the preferred embodiment constructed in accordance with the principles of the present invention utilize a computer and are described herein as implemented by logical operations performed by a computer. The logical operations of these various computer implemented processes are generally performed either (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 6:
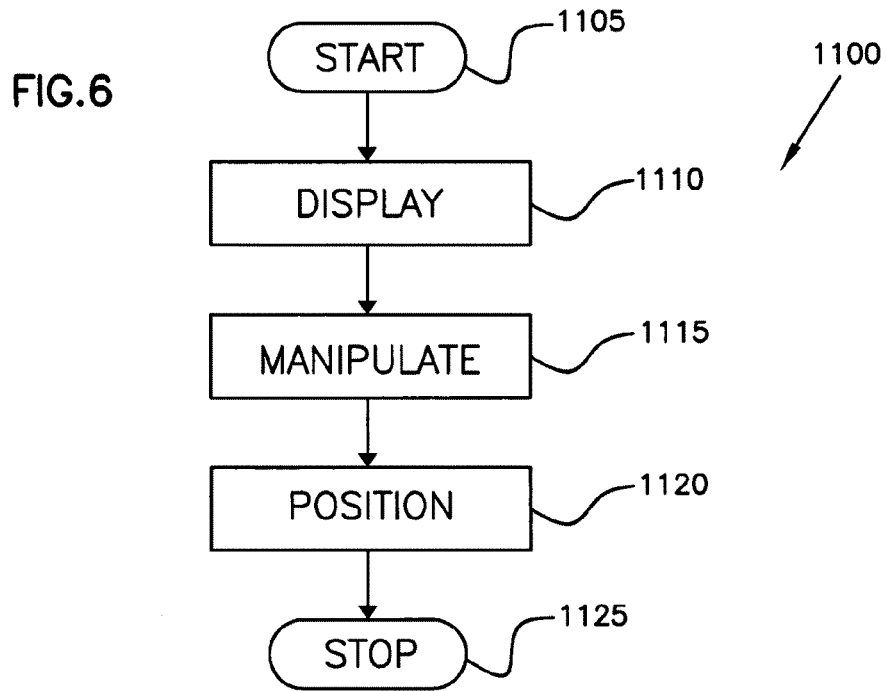
FIG. 6 illustrates an operational flow for implementing the plan operation of the creation process of FIG. 1.

Referring now to FIG. 6, an example process 1100 for implementing the plan operation 1015 of FIG. 1 is disclosed. The process 1100 begins at start operation 1105 and proceeds to a display operation 1110. The display operation 1110 displays at least a portion of the electronic model 100 of the patient's dentition in a pre-treatment arrangement (e.g., see FIG. 3). A manipulate operation 1115 then shifts each individual tooth 110 to a desired position (e.g., see FIG. 4). In certain embodiments, shifting a tooth 110 includes modifying the rotation, the tip orientation, and/or the torque orientation of the tooth 110. In an embodiment, the tooth 110 can be shifted about six degrees of freedom.

Figure 7A:
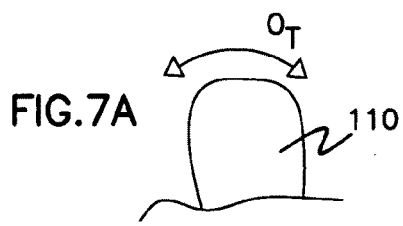
FIG. 7A is a front view of a tooth showing the arc over which the tooth can tip is a mesial or distal direction according to one embodiment of the present disclosure.
Figure 7B:
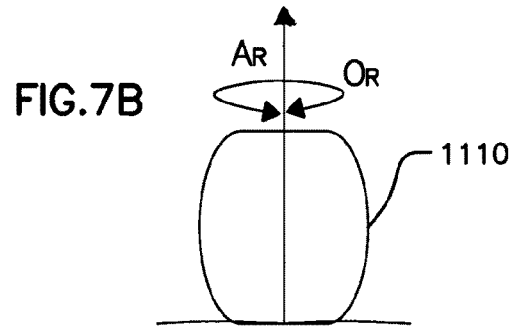
FIG. 7B is a front view of a tooth showing how the tooth can rotate according to one embodiment of the present disclosure.
Figure 8:
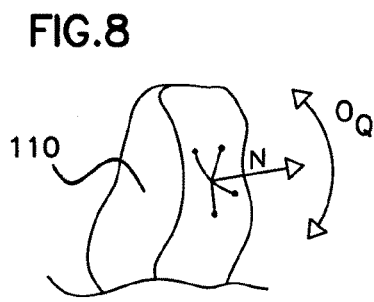
FIG. 8 is a front perspective view of a tooth showing how the arc over which the tooth can torque in a facial or lingual direction according to one embodiment of the present disclosure.

FIGS. 7(A-B) are front views and FIG. 8 is a front perspective view of an example tooth 110. As shown in FIG. 7A, modifying the tip orientation (i.e., yaw) of the tooth 110 includes tilting the tooth 110 in either a mesial direction or a distal direction along a first arc $O_T$. Rotating the tooth 110 includes turning the tooth 110 about an axis of rotation $A_R$ to move one side of the tooth in a buccal/labial direction and the other side of the tooth in a lingual direction as shown in FIG. 7B. As shown in FIG. 8, modifying the torque orientation (i.e., pitch) of the tooth 110 includes tilting the tooth 110 in either a lingual direction or a facial direction along a second arc $O_Q$.

Figure 9:
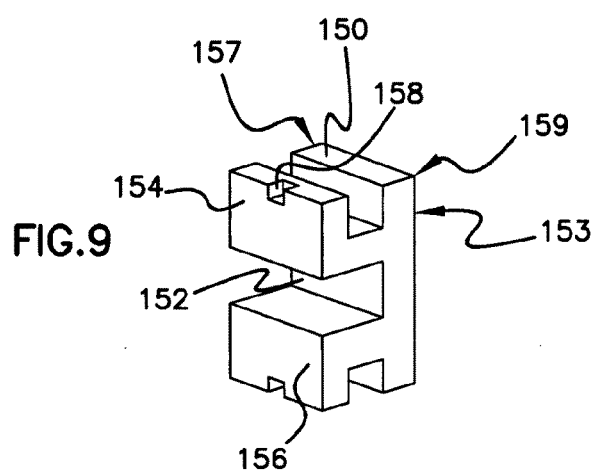
FIG. 9 is a front perspective view of a bracket according to one embodiment of the present disclosure.

When the teeth have been arranged into a desired post-treatment arrangement, a position operation 1120 determines a position on the surface of one or more teeth 110' in the electronic model 100 for an electronic model of a bracket 150 (FIG. 9). In general, the position of the bracket 150 includes at least four components: an occlusal-apical component OA; a medial-distal component MD; a tip orientation θ1; and a torque orientation θ2. The process 1100 ends at stop module 1125.

Referring to FIG. 9, one example of a bracket 150 configured to mount to a tooth 110' is shown. The bracket 150 includes a front 151, a back 153, a first side 157, and a second side 159. The front 151 of the bracket 150 includes a recess 152 defined between a first section 154 and a second section 156. In general, the recess is configured to receive an arch wire. An arch wire is a wire that extends around a dental arch and couples to the recess 152 of each bracket 150 along the dental arch. The recess 152 extends in a substantially linear path from the first side 157 to the second side 159. The first and second sections 154, 156 each include indicia 158 indicating an approximate midpoint between the first side 157 and the second side 159.

Figure 10:
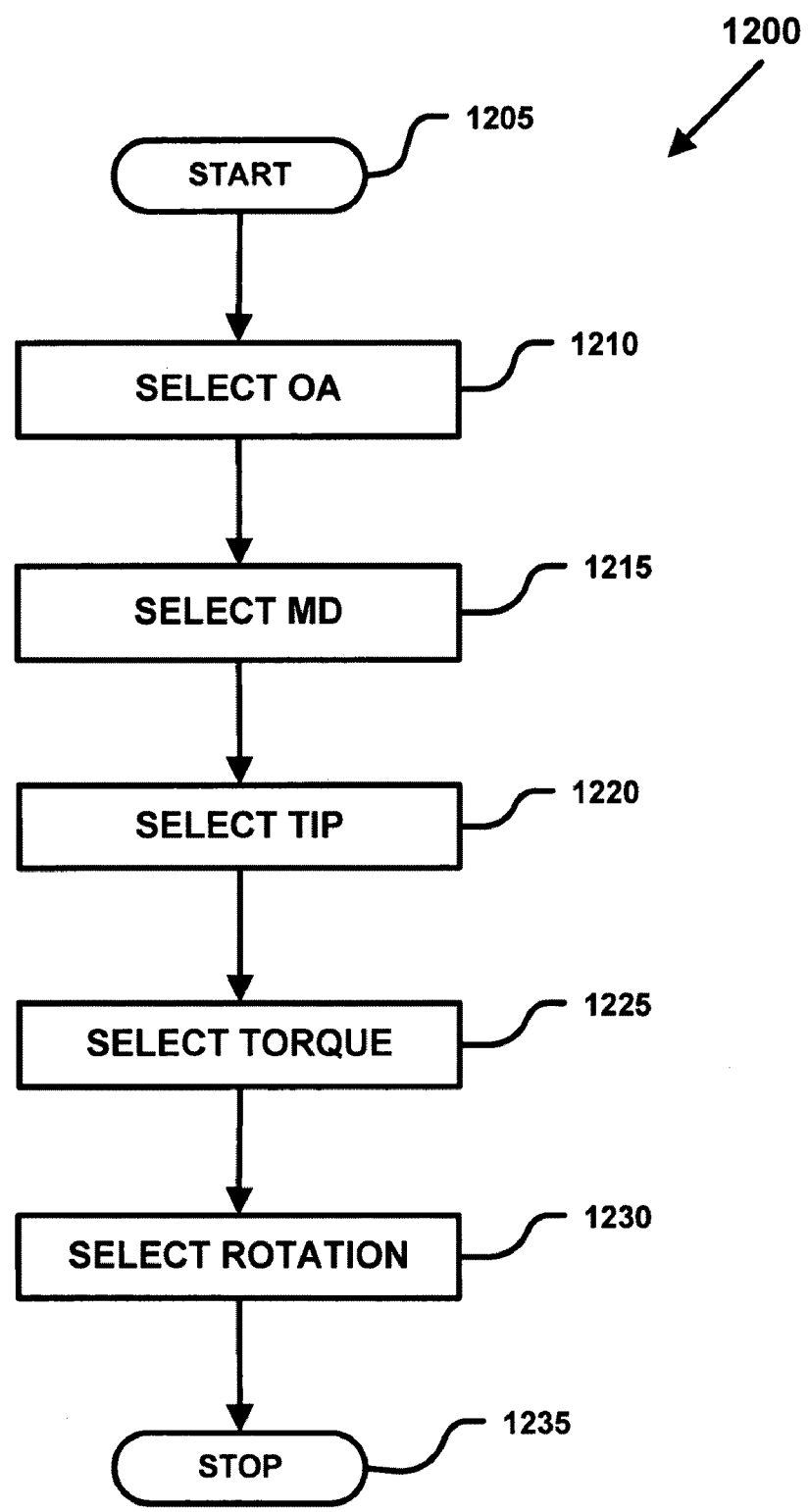
FIG. 10 illustrates an operation flow for an example process for determining the desired positions of brackets on teeth in a post-treatment position according to one embodiment of the present disclosure.

Referring now to FIG. 10, an example process 1200 for determining the desired positions of brackets 150 on teeth 110' is disclosed. The process 1200 begins at start operation 1205 and proceeds to a first select operation 1210. The first select operation 1210 determines an occlusal-apical position OA of each tooth 110' (see FIG. 11). The occlusal-apical position OA specifies the position of the bracket 150 on the clinical crown between the occlusal surface of the tooth 110' and the gingival border.

Figure 11:
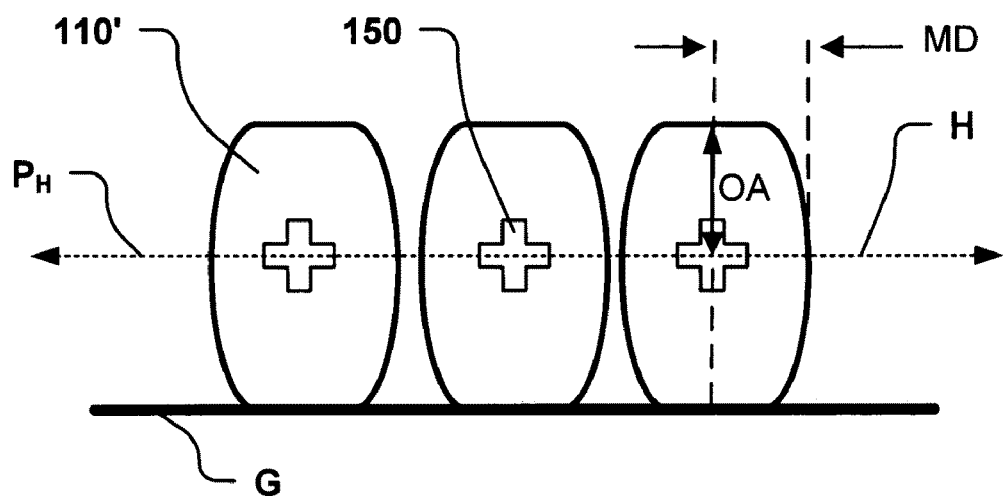
FIG. 11 is a front view of brackets arranged into desired positions on teeth arranged in post-treatment positions according to one embodiment of the present disclosure.

In a preferred embodiment, the first select operation 1210 determines the occlusal-apical position OA of each bracket 150 by determining an arch wire path H (see FIG. 11). Typically, the path H followed by the arch wire at the end of the treatment extends along a generally horizontal plane $P_H$ that cuts through the clinical crown of each tooth 110' (see FIG. 11). In some embodiments, the generally horizontal plane $P_H$ is substantially parallel to the Frankfort horizontal plane. In other embodiments, the plane $P_H$ is curved to follow the curve of Wilson and/or the curve or Spee.

A second select operation 1215 determines a medial-distal position MD for each bracket 150. In certain embodiments, the mesial-distal component MD refers to a distance from the bracket 150 to either the mesial or the distal side of the tooth 110'. In a preferred embodiment, the mesial-distal component MD refers to the distance from the indicia 158 (FIG. 9) of the bracket 150 to one of the sides of the tooth 110'. Typically, a bracket 150 is generally centered between the mesial side and the distal side of the tooth 110'.

A third select operation 1220 determines a tip orientation $\theta_1$ of each bracket 150. The tip orientation $\theta_1$ refers to the degree to which each bracket 150 tilts along the arc $O_T$ (FIG. 7) of the tooth 110'. For example, in one embodiment, the tip orientation indicates the angle $\theta_1$ between a line extending along the recess 152 of the bracket 150 and the substantially horizontal plane $P_H$. Typically, when the brackets 150 are mounted on teeth 110' arranged in a post-treatment position, the tip orientation $\theta_1$ should approach or equal zero (see FIG. 11).

A fourth select operation 1225 determines a torque orientation $\theta_2$ of each bracket 150. The torque orientation $\theta_2$ refers to the degree to which a normal vector $N_B$ (FIG. 13) of each bracket 150 tilts along the arc $O_Q$ (FIG. 8) of the tooth 110' relative to the normal vector $N_T$ of each tooth 110' (FIG. 13). The torque orientation $\theta_2$ of the bracket 150 can be adjusted by modifying the amount and placement of adhesive 130 (FIG. 12). Typically, when the brackets 150 are mounted on teeth 110' arranged in a post-treatment position, the normal vector NB of the bracket 150 should be generally parallel to the substantially horizontal plane $P_H$ (e.g., see FIG. 12). The process 1200 ends at stop operation 1230.

A fifth select operation 1230 determines a rotational orientation about an axis $\theta_R$ of each bracket 150. The rotational orientation refers to the arrangement of the bracket 150 about the axis of rotation $\theta_R$, which is generally parallel with the axis of rotation $A_R$ of the corresponding tooth 110 (see FIG. 7B). Adjusting the rotational orientation of a bracket 150 adjusts how the sides of the bracket 150 interact with the corresponding tooth 110. For example, rotating the bracket 150 in a first direction can raise a first side of the bracket off the tooth 110 and press an opposite side of the bracket onto the tooth 110.

Figure 14:
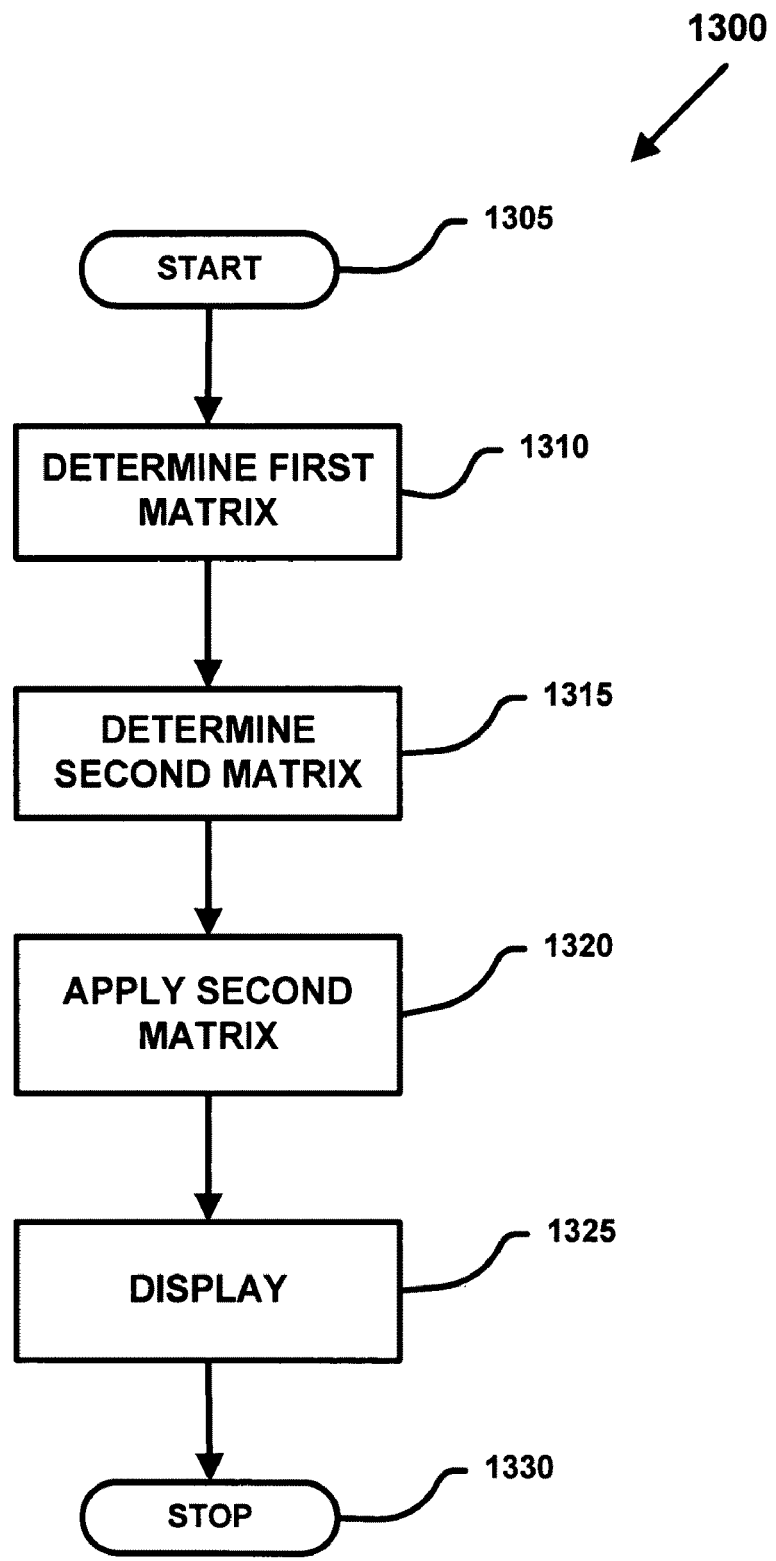
FIG. 14 illustrates an operation flow for an example process for determining the desired positions of brackets on a pre-treatment arrangement of teeth according to one embodiment of the present disclosure.

Referring now to FIGS. 14-16, desired bracket positions on the pre-treatment arrangement of teeth 110 can be determined based on the selected bracket positions on the post-treatment arrangement of teeth 110'. FIG. 14 illustrates an example process 1300 for determining the desired positions of brackets 150 on a pre-treatment arrangement of teeth 110. The process 1300 begins at start operation 1305 and proceeds to a first formation operation 1310. The first formation operation 1310 creates at least a first transformation matrix to describe the shift in position of the teeth 110 of the electronic model 100 from the pre-treatment arrangement to the post-treatment arrangement. In one embodiment, the first formation operation 1310 generates at least a first transformation matrix for each tooth 110.

In general, the first transformation matrix represents the transition in space of one or more teeth 110 in the electronic model 100. In a preferred embodiment, the transformation matrix is generated as a four-by-four identity matrix created based on known algorithms. As the teeth 110 are manipulated from a pre-treatment position to a post-treatment position, the first transformation matrix is updated such that multiplying the first matrix by the positions of the teeth 110 in the pre-treatment configuration will produce the post-manipulation positions of the teeth 110.

A second formation operation 1315 creates a second transformation matrix (i.e., an inverse matrix). The second transformation matrix represents the transition of the teeth 110 from the post-treatment arrangement to the pre-treatment arrangement. In one embodiment, the second transformation matrix is generated based on the first transformation matrix according to known algorithms. In another embodiment, the second transformation matrix is formed prior to manipulating the teeth 110 and is updated along with the first matrix as the teeth are manipulated.

A transform operation 1320 applies the second set of transformation matrices to the bracket positions of the post-treatment teeth 110' to obtain desired pre-treatment bracket positions. A display operation 1325 renders electronic models of the brackets 150 in the pre-treatment positions and superimposes the brackets 150 on a pre-treatment arrangement of the teeth 110 (See FIG. 15). The process ends at stop operation 1330. Further information regarding the formation and use of transformation matrices can be found in the U.S. application Ser. No. 11/231,064 entitled "System and Method for Determining Condyle Displacement Utilizing Electronic Models of Dental Impressions Having a Common Coordinate System," filed Sep. 19, 2005, the disclosure of which is hereby incorporated by reference.

Figure 17:
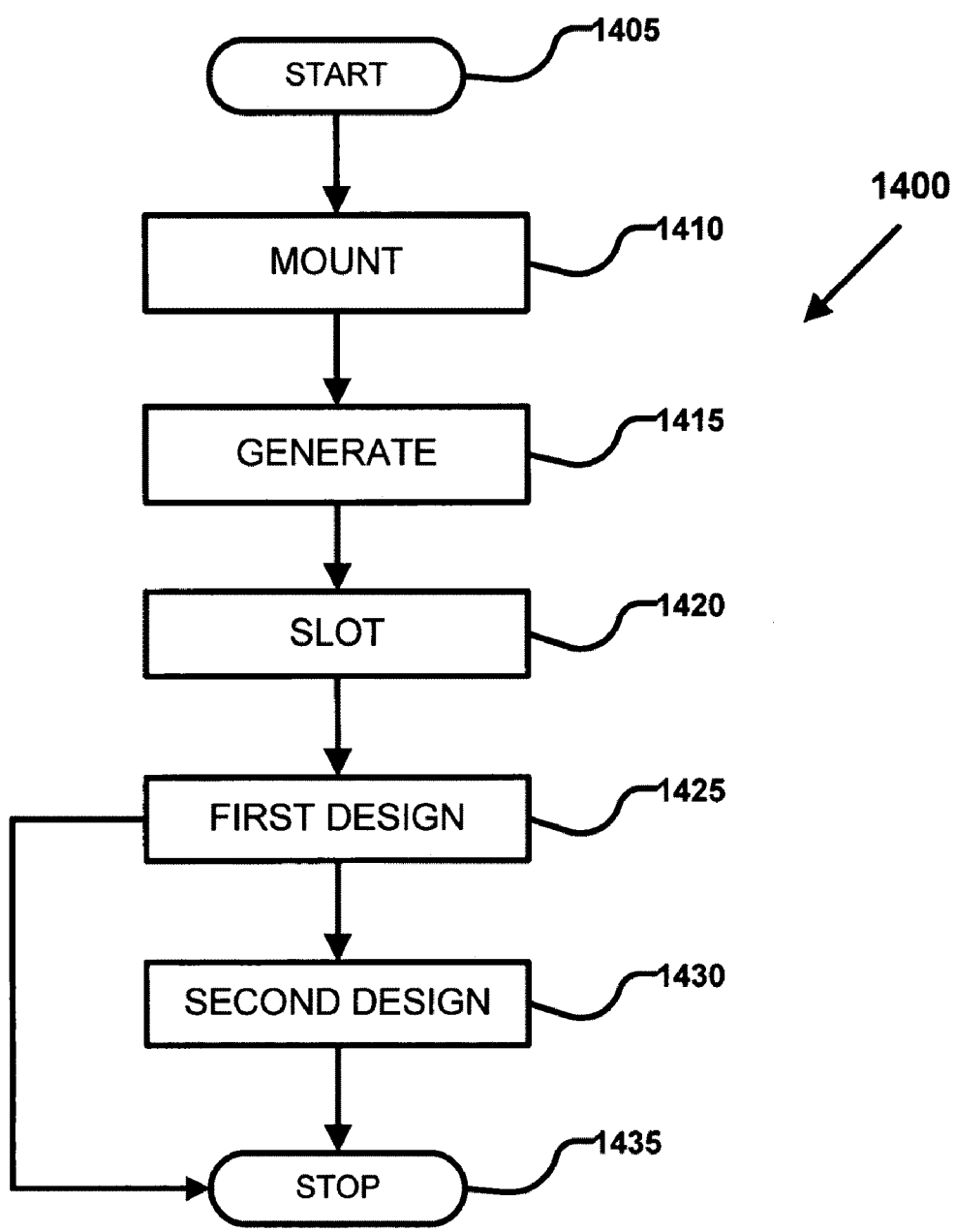
FIG. 17 illustrates an operation flow for a generation process of an electronic model of an alignment device according to one embodiment of the present disclosure.

Referring now to FIGS. 17-20, electronic models of alignment devices can be designed to facilitate accurate placement of brackets into the desired pre-treatment positions. One example alignment device is illustrated in FIGS. 17-23. FIG. 17 illustrates an operation flow for a generation process 1400 for creating an electronic model 300 of an alignment device 310. The generation process 1400 begins at a start operation 1405 and proceeds to a mounting operation 1410. The mounting operation 1410 superimposes electronic models of brackets 150 into desired pre-treatment positions on the electronic model 100 of the patient's teeth 110 (e.g., see FIG. 15).

A generate operation 1415 creates an electronic model 300 of a body 312 of an alignment device 310 configured to mount over one or more teeth 110 of the electronic model 100. In general, the generate operation 1415 forms the body 312 to extend from the front of a tooth 110, over the occlusal surface of the tooth 110, and partially over the back of the tooth 110 (e.g., see FIG. 20). In a preferred embodiment, the body 312 is configured to extend continuously away from the surface of the tooth 110 without undercuts, thereby facilitating mounting of the alignment device 310 on the tooth 110 (e.g., see FIG. 20).

In some embodiments, the body 312 is configured to mount over substantially all of the teeth 110 in the dental arch of either the mandible or the maxilla. In other embodiments, the body 312 is configured to mount over only one tooth 110 (e.g., see FIG. 19). For clarity, FIG. 18 illustrates an electronic model 300 of an alignment device 310 configured to mount over three adjacent teeth. The model 300 is shown superimposed over electronic models of a first tooth 112, a second tooth 114, and a third tooth 116.

A slot operation 1420 defines one or more openings 314 in the body 312 (FIG. 18). Each of the openings 314 is configured to enable placement of a bracket 150 through the slot 314 and onto the surface of the tooth 110. Typically, the body 312 defines an opening 314 for each tooth 110 to which the body 312 is configured to couple. In the example shown in FIG. 18, the body 312 defines three openings 314.

A first design operation 1425 creates at least one orientation indicator 320 on the body 312 adjacent each opening 314. In general, the orientation indicator 320 is configured to indicate a desired occlusal-apical position OA, a desire tip orientation $\theta_1$, and a desired torque orientation $\theta_2$ at which a bracket 150 should be mounted to a tooth 110 through each opening 314. In certain embodiments, the first design operation 1425 includes forming a first member 324 and a second member 326 to protrude from the body 312 (FIG. 19). The first member 324 is spaced from the second member 326 to form a channel 322 therebetween (see FIG. 20).

In certain embodiments, the members 324, 326 and the channel 322 are configured to align with the sections 154, 156 and the recess 152, respectively, of each bracket 150. Aligning the channel 322 with the recess 152 includes positioning the members 324, 326 to form the channel at the occlusal-apical position OA of the bracket recess 152. Furthermore, aligning the members 324, 326 with the sections 154, 156 includes positioning the members 324, 326 at the same tilt orientation $\theta_1$ or tip orientation $\theta_2$ as sections 154, 156 of the bracket 150 when the bracket 150 is positioned in a post-treatment arrangement. By so aligning the orientation indicator 320 of the alignment device 310, the orientation indicator 320 of a fabricated alignment device 310 can provide guidance in determining the desired position of a bracket 150 on a physical tooth 110.

In some embodiments, the first design operation 1425 forms the orientation indicator 320 to extend the entire length between the slot openings 314 defined by the body 312 (e.g., see FIG. 18). In other embodiments, the first design operation 1425 forms an orientation indicator 320 to extend a relatively short distance away from each slot opening 314 (e.g., see FIG. 19). In such an embodiment, the first design operation 1425 can form an orientation indicator 320 on either side of an opening 314 (FIG. 19) or on only one side of each opening 314.

From the first design operation 1425, the process 1400 can either end at stop operation 1435 or can proceed to a second design operation 1430. The second design operation 1430 forms a mesial-distal indicator 318 on the body 312 (FIG. 19). In general, the second design operation 1430 forms the mesial-distal indicator 318 to align with the midpoint indicia 158 of the bracket 150 when the bracket 150 is properly positioned on the tooth 110. In a preferred embodiment, the mesial-distal indicator 318 includes a notch defined in the body 312 above the slot 314. The generation process 1400 ends at stop operation 1435.

An alignment device 310 can be fabricated based on the electronic model 300. In certain embodiments, the electronic model 300 of the alignment device 310 (or data obtained from the electronic model 300) can be forwarded from the computing system 220 on which the model 300 was generated to a fabrication device 270 (FIG. 5). The fabrication device 270 produces a physical alignment device 310. For example, the fabrication device 270 can rapidly print the alignment device 310 from at least one of wax, thermoplastic, ceramic, rubber, and metal. In one embodiment, the alignment device 310 is fabricated from a bio-compatible material, such as an ABS material.

Figure 21:
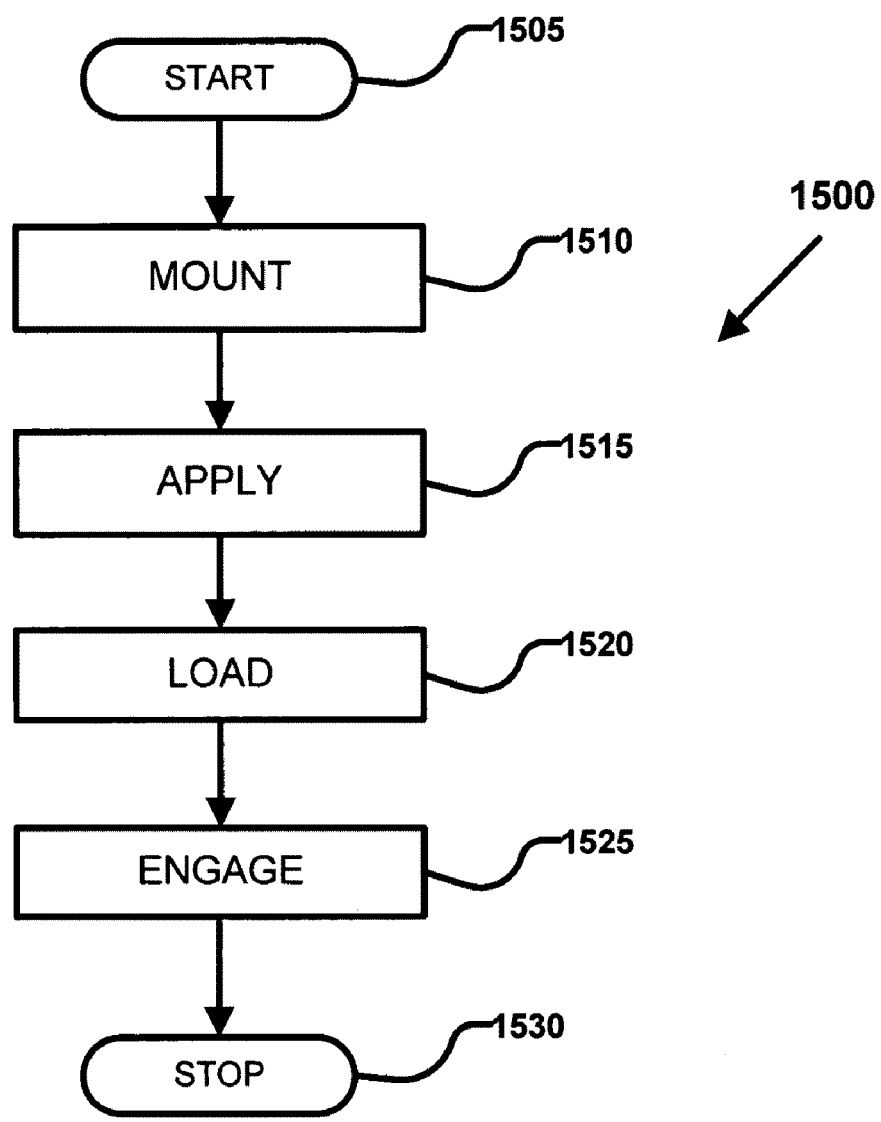
FIG. 21 illustrates an example operation flow for an alignment process using a fabricated first alignment device to position a bracket according to one embodiment of the present disclosure.

FIG. 21 illustrates an example operational flow for an alignment process 1500 using a fabricated alignment device 310 to position a bracket 150 on a surface. For example, the alignment device 310 can facilitate positioning a bracket 150 on a dental cast representing the teeth of a patient. In other embodiments, the alignment device 310 can also facilitate positioning a bracket 150 on a tooth 110 of a patient. The alignment device 310 enables the bracket to be positioned along six degrees of movement.

The alignment process 1500 begins at a start operation 1505 and proceeds to a mounting operation 1510. The mounting operation 1510 positions the alignment device 310 on one or more teeth 110 of the patient (i.e., or on physical representations of the teeth). The teeth 110 are typically arranged in the pre-treatment position (see FIG. 18). An apply operation 1515 administers adhesive 130 (FIG. 22) to the back 153 of a bracket 150. The adhesive 130 is applied to secure the bracket 150 to the tooth 110. Examples of adhesive 130 include resin, resin-based adhesive, composite cement, glass ionomer, and polycarboxylate. When a bracket 150 is mounted to a physical representation of a tooth, the adhesive holding the bracket 150 to the representation solidifies on the bracket 150 to form a custom pad (see reference number 130 in FIGS. 12 and 13) and is eventually mounted to the actual tooth 110 of the patient as part of the bracket 150.

Figure 22:
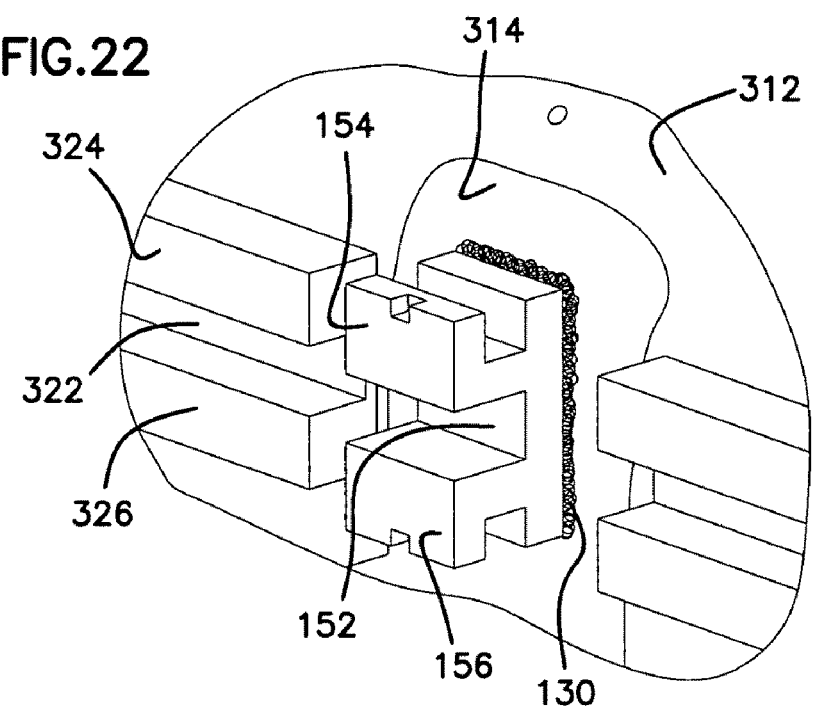
FIG. 22 is a partial, front perspective view of a bracket positioned within the recess of the alignment device of FIG. 19 according to one embodiment of the present invention.

A load operation 1520 mounts the bracket 150 to the tooth surface using the adhesive 130 (see FIG. 22). The general occlusal-apical position $O_A$, mesial-distal position MD, rotational orientation, tip orientation $\theta_1$, and torque orientation $\theta_2$ can be estimated by a user. For example, the user can align the recess 152 and the indicia 158 on the bracket 150 with the channel 322 and the mesial-distal indicator 318 on the indicator 310 by sight. In an alternative embodiment, the load operation 1520 can mount the bracket 150 by loading the bracket 150 onto an alignment tool 350 and pressing the back 153 of the bracket 150 against the tooth surface through the opening 314 in the alignment device 310.

Figure 23:
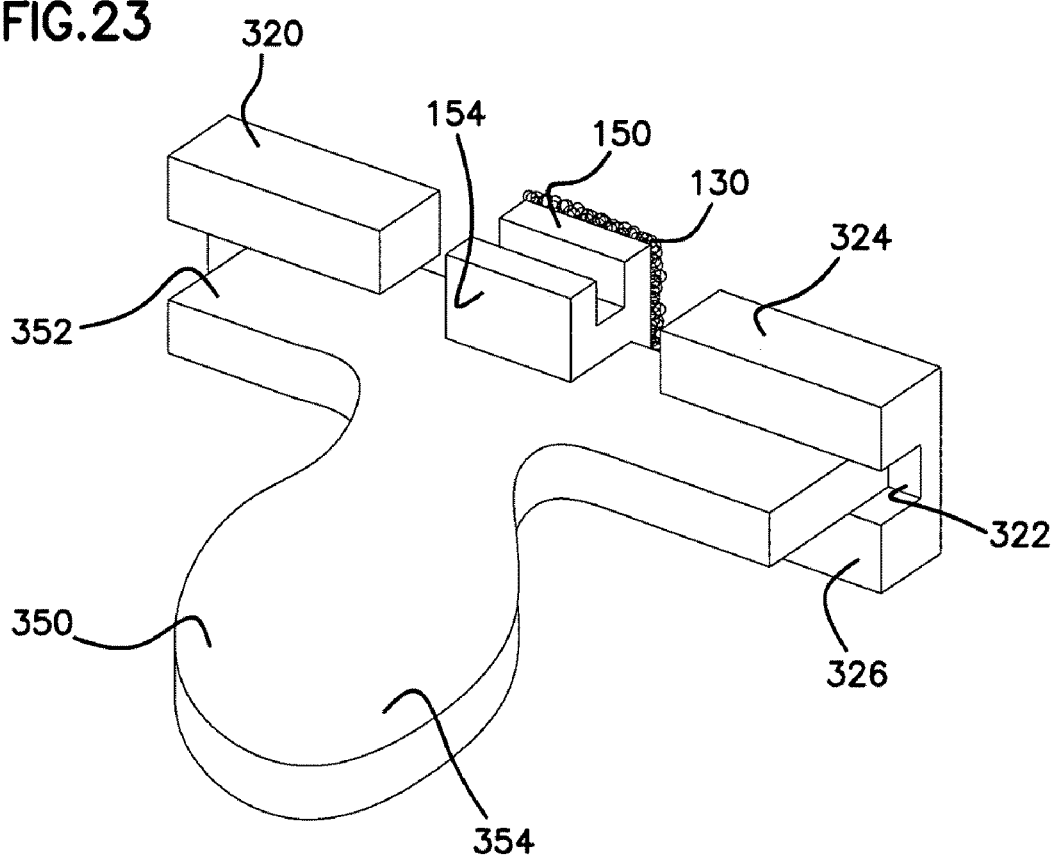
FIG. 23 is a front, perspective view of an alignment tool engaging a bracket and an orientation indicator of the alignment device of FIG. 19 in which the body of the alignment device has been removed for clarity.

A secure operation 1525 fine-tunes the position of the bracket 150 on the tooth surface along the six degrees of freedom by inserting an alignment tool 350 into both the recess 152 and the channel 322 (see FIG. 23). For example, inserting the tool 350 also adjusts the torque orientation $\theta_2$ of the bracket 150 to match the torque orientation of the channel 322. Light pressure can be applied to the bracket 150 via the tool 350 to hold the bracket 150 in place while the adhesive 160 sets or cures. The alignment process ends at stop module 1530. If the brackets 150 were aligned on physical representations of the teeth instead of the patient's actual teeth, then the brackets 150 can be used in forming an indirect bonding tray for loading the brackets 150 onto the actual teeth.

FIG. 23 illustrates one example of an alignment tool 350 engaging a bracket 150 and an orientation indicator 320. The alignment tool 350 includes an engagement member 352 and a handle 354. The engagement member 352 has a length sufficient to extend at least partially across the bracket 150 and at least partially across the orientation member 320. The engagement member 352 also has a transverse cross-section shaped to enable the engagement member 352 to be received within the recess 152 defined in the bracket 150 and within the channel 322 of the alignment device 310.

Referring now to FIGS. 24-29, a second embodiment of an alignment device 410 is disclosed. In one embodiment, the second alignment device 410 can be configured to mount multiple brackets 150 directly to a patient's teeth 110 simultaneously, thereby reducing the amount of time a patient must spend having the brackets 150 installed during the clinical bonding process (e.g., see FIG. 28). In another embodiment, the second alignment device 410 can be configured to mount a single bracket 150 directly to a single tooth 110 (e.g., see FIG. 25). In other embodiments, however, the second alignment device 410 can be used to mount one or more brackets 150 to a dental cast for use in indirect bonding.

The second alignment device 410 includes a body 412 defining an opening 414 (see FIG. 24). The second alignment device 410 also includes an orientation indicator 420 enabling a user to couple a brackets 150 into a desired position within each opening 414 of the second alignment device 410. In certain embodiments, the orientation indicator 420 includes one or more fingers 422 protruding into the opening 414 from the body 412. In a preferred embodiment, the alignment device 410 includes three fingers 422. Each finger 422 can have a fingertip configured to engage (e.g., be received within) a notch or recess in the bracket 150.

In the example shown in FIG. 25, the recess 152 of each bracket 150 is retained in a desired occlusal-apical position, tip orientation, and tilt orientation by a first fingertip 424 coupled to a finger 422 extending from one side of the opening 414 and by a second fingertip 426 coupled to a finger 422 extending from the opposite side of the opening 414 (see FIG. 25). In other embodiments, however, the brackets recess 152 can be supported using only one fingertip 424. A third fingertip 428 can retain the bracket 150 in a desired mesial-distal position by engaging the indicia 158 of the bracket 150 (see FIG. 25).

In general, the fingertips 424, 426, 428 are sized to securely engage and retain the bracket 150. As shown in FIG. 25, the fingertips 424, 426 and the fingertip 428 can have substantially the same dimensions of the recess 152 and the indicia 158, respectively. For example, in some embodiments, each of fingertips 424 and 426 is configured to extend along substantially half of the bracket recess 152. In other embodiments, however, each of the fingertips 424 and 426 extends only partially along the bracket recess 152.

The second alignment device 410 can be fabricated from an electronic model using a rapid prototyping machine. For example, the alignment device 410 can be printed from the same materials disclosed above with respect to fabrication of the first alignment device 310. This prototyping technique, however, is meant to be illustrative only and other suitable fabrication techniques can also be used.

Figure 26:
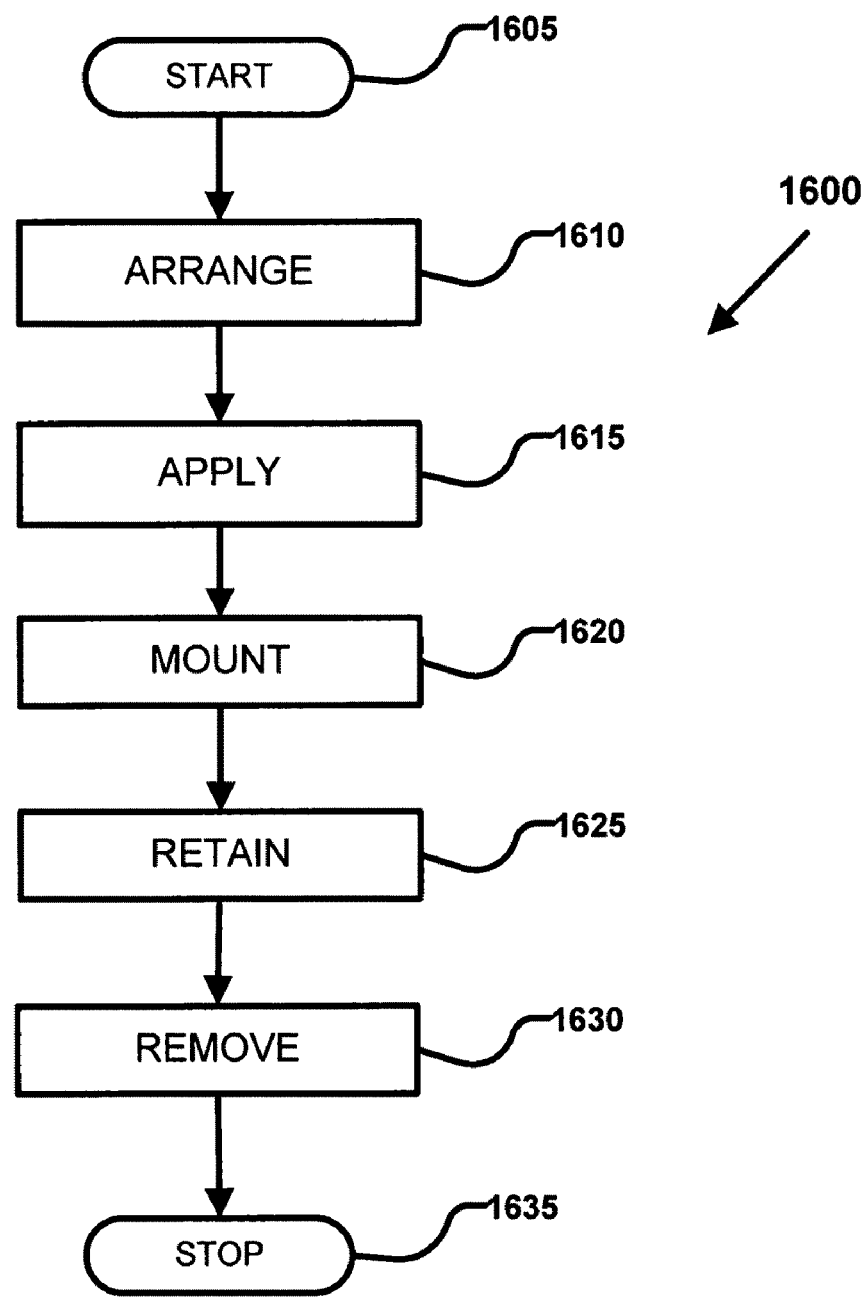
FIG. 26 illustrates an operation flow for a bracket securement process by which one or more brackets can be secured to teeth using the second alignment device according to one embodiment of the present disclosure.
Figure 27:
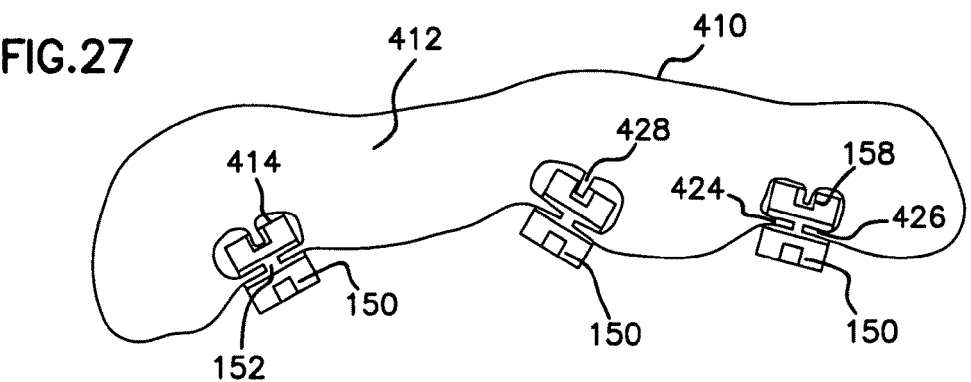
FIG. 27 is a front view of three brackets coupled to a second alignment device configured to mount to three teeth according to one embodiment of the present disclosure.
Figure 28:
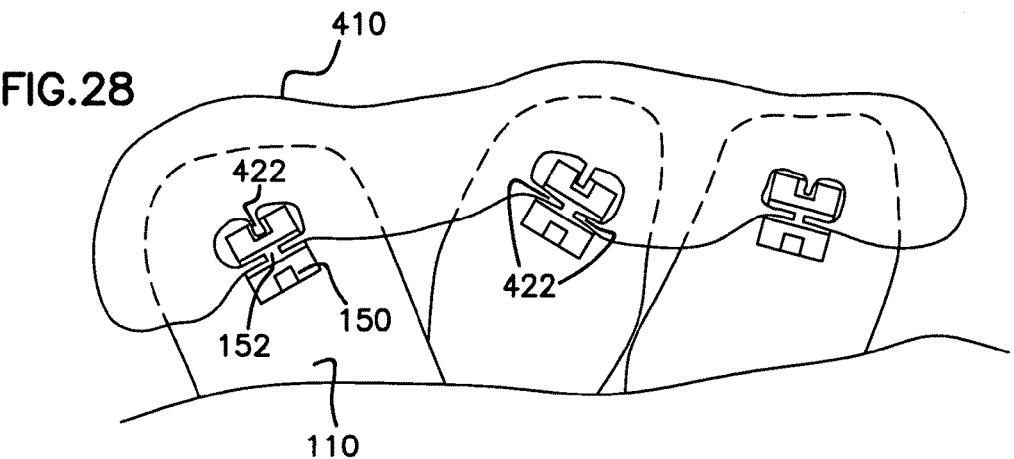
FIG. 28 shows the brackets and second alignment device of FIG. 27 mounted to three teeth.
Figure 29:
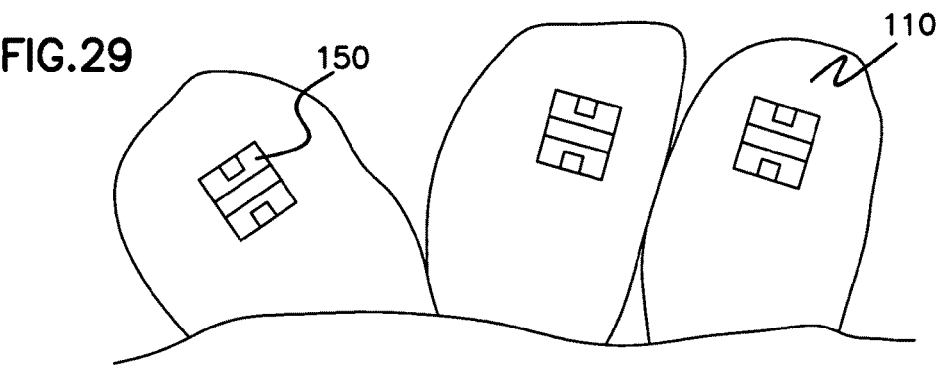
FIG. 29 illustrates three teeth on which brackets are mounted in desired pre-treatment positions according to one embodiment of the present disclosure.

FIG. 26 illustrates an operation flow for a bracket securement process 1600 by which one or more brackets 150 can be secured to teeth using the second alignment device 410. FIGS. 27-29 illustrate the results of different steps in the process 1600. The securement process 1600 begins at start operation 1605 and proceeds to an arrange operation 1610. The arrange operation 1610 couples one or more brackets 150 to the second alignment device 410.

FIG. 27 illustrates the result of the arrange operation 1610. As shown in FIG. 27, the second alignment device 410 includes a body 412 configured to mount over three teeth 110. Three brackets 150 are coupled to fingers 422 protruding from the body 412 of the second alignment device 410. Fingertips 424, 426 engage the recesses 152 of the brackets 150 and fingertips 428 engage the indicia notches 158 of the brackets 150.

An apply operation 1615 administers adhesive (not shown) either to the back 153 of the brackets 150 or to the surface of the teeth 110. In another embodiment, adhesive can be applied to both the brackets 150 and the teeth 110. A mount operation 1620 couples the alignment device 410 to the teeth 110 of the patient (i.e., or to the physical representation of the teeth 110). When a bracket 150 is mounted to a physical representation of a tooth, the adhesive holding the bracket 150 to the representation solidifies on the bracket 150 to form a custom pad (see reference number 130 in FIGS. 12 and 13) and is eventually mounted to the actual tooth 110 of the patient as part of the bracket 150.

FIG. 28 illustrates the result of the mount operation 1620. The second alignment device 410 is coupled to the three teeth 110 of the patient. The brackets 150 are held at desired positions on the teeth. In particular, each bracket 150 is retained at a desired occlusal-apical position, a desired mesial-distal position, a desired tip orientation, and a desired torque orientation. In other embodiments, the mount operation 1620 can mount the alignment device 410 on the teeth 110 before the arrange operation 1610 couples the brackets 150 to the alignment device 410.

A retain operation 1625 holds the brackets 150 to the teeth 110 for a sufficient amount of time to enable the adhesive to set or cure. When the brackets 150 are bound to the teeth 110 with sufficient strength, a remove operation 1630 detaches the fingers 422 from the brackets 150. For example, in one embodiment, the fingers 422 are resilient and the remove operation 1630 bends the fingers 422 away from the brackets. In another embodiment, the remove operation 1630 pulls the alignment device 410 away from the front 151 of the brackets 150. The securement process 1600 ends at stop operation 1635.

FIG. 29 shows the brackets 150 secured to the teeth 110 arranged in a pre-treatment position. The brackets 150 shown are ready to receive an arch wire or to otherwise begin treatment.

Although embodiments of the present disclosure have been described with respect to digitizing a dental cast of a patient, it should be appreciated that the principles of the present disclosure can also be applied to a digitized impression or a direct scan of the dentition of a patient. In the former case, a computer can invert the scanned impression to provide a positive image of the patient's teeth.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

What is claimed is:

1. An alignment device for positioning at least a first bracket on at least a first tooth, the first bracket defining a recess, the alignment device comprising:
   a body configured to couple to a surface, the body defining at least one slot that is configured to enable placement of at least the first bracket at a location on the surface through the slot;
   an orientation indicator coupled to the body adjacent the slot, the orientation indicator including a first member and a second member protruding from the body adjacent the slot to define at least one channel, the first and second members being configured to indicate a desired torque orientation of the first bracket to be placed at the location on the surface through the slot; and
   an alignment tool configured to align the first bracket with the orientation indicator when the alignment tool is inserted into the channel of the orientation indicator and the recess of the first bracket when the first bracket is positioned at the location on the surface through the slot.

2. The alignment device of claim 1, wherein the body is configured to couple to a plurality of teeth of a dental cast of a patient.

3. The alignment device of claim 1, further comprising a plurality of slots defined by the body, each slot configured to enable placement of one of a plurality of brackets.

4. The alignment device of claim 3, further comprising a plurality of orientation indicators, each orientation indicator being positioned adjacent to at least one of the slots.

5. The alignment device of claim 4, wherein each orientation indicator extends between two adjacent slots defined in the body.

6. The alignment device of claim 1, wherein the channel is shaped and oriented to indicate a desired tip orientation of the first bracket.

7. The alignment device of claim 1, wherein the channel is shaped and oriented to indicate a desired torque orientation of the first bracket.

8. The alignment device of claim 1, further comprising a mesial-distal indicator configured to denote a desired mesial-distal position of the first bracket.

9. The alignment device of claim 1, wherein the body is formed from a wax material.

10. The alignment device of claim 1, wherein the channel defined by the orientation indicator aligns along a common axis with the recess of the first bracket.

11. The alignment device of claim 1, wherein the orientation indicator is a first orientation indicator, and wherein the alignment device further comprises a second orientation indicator coupled to the body adjacent the slot, the second orientation indicator being positioned on an opposite side of the slot from the first orientation indicator.

12. The alignment device of claim 11, wherein the second orientation indicator includes a first member and a second member protruding from the body to define at least one channel that aligns with the channel of the first orientation indicator.

* * * * *